United States Patent
Atsumi et al.

[11] 3,950,346
[45] Apr. 13, 1976

[54] NOVEL PROCESS FOR PRODUCING 2-KETOETHYLBENZOMORPHAN DERIVATIVES AND SALTS THEREOF

[75] Inventors: Toshio Atsumi, Ooi; Kenji Kobayashi; Yoshiaki Takebayashi, both of Takarazuka; Hisao Yamamoto, Nishinomiya, all of Japan

[73] Assignee: Sumitomo Chemical Company, Limited, Japan

[22] Filed: May 3, 1973

[21] Appl. No.: 356,807

[30] Foreign Application Priority Data
May 8, 1972 Japan.............................. 47-45683

[52] U.S. Cl. ...... 260/293.54; 260/DIG. 13; 424/267
[51] Int. Cl.[2].................................... C07D 221/26
[58] Field of Search................. 260/293.54, DIG. 13

[56] References Cited
UNITED STATES PATENTS

| | | | |
|---|---|---|---|
| 3,045,023 | 7/1962 | Rorig............................. | 260/293.78 |
| 3,138,603 | 6/1964 | May................................. | 260/294.3 |
| 3,502,688 | 3/1970 | Berger et al. ...................... | 260/295 |
| 3,639,407 | 2/1972 | Clarke et al. .................. | 260/293.54 |
| 3,733,330 | 5/1973 | Schubert et al................ | 260/293.54 |

*Primary Examiner*—G. Thomas Todd
*Attorney, Agent, or Firm*—Craig & Antonelli

[57] ABSTRACT

2-Ketoethyl-6,7-benzomorphan derivatives of the formula:

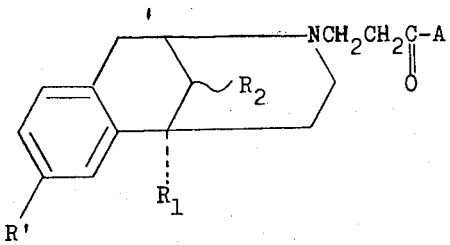

and their pharmaceutically acceptable non-toxic salts, which are useful as non-addictive analgesics and pain-relieving agents and can be prepared by reacting the corresponding 6,7-benzomorphan derivative of the formula:

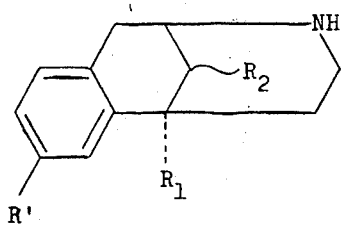

with a vinyl carbonyl compound of the formula:

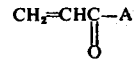

[wherein R' is a hydrogen atom or a group of the formula: —OR" (wherein R" is a hydrogen atom, an alkanoyl group, an alkyl group, an aralkyl group, an alkoxycarbonylmethyl group or a tetrahydropyranyl group), $R_1$ is a hydrogen atom, an alkyl group or a substituted or unsubstituted aryl group, $R_2$ is a hydrogen atom or an alkyl group and A is an alkyl group, an alkoxy group, a substituted or unsubstituted aryl group or a substituted or unsubstituted amino group].

20 Claims, No Drawings

NOVEL PROCESS FOR PRODUCING 2-KETOETHYLBENZOMORPHAN DERIVATIVES AND SALTS THEREOF

The present invention relates to 2-ketoethyl-6,7-benzomorphan derivatives and their pharmaceutically acceptable non-toxic salts, which are useful as non-addictive analgesics and pain-relieving agents, and their production and compositions containing them.

Hitherto, many benzomorphan derivatives (e.g. phenazocine, pentazocine) have been developed as analgesic drugs but most of them have addiction and produce narcotic symptoms. The compounds of the present invention do not show any drug dependency in animal test.

A basic object of the present invention is to provide a novel process for producing known and new pharmacologically active 2-ketoethyl-6,7-benzomorphan derivatives. Another object of this invention is to provide novel 2ketoethyl-6,7-benzomorphan derivatives, which are per se useful as analgesic agents. A further object of the invention is to provide pharmaceutical compositions containing novel 2-ketoethyl-6,7-benzomorphan derivatives. These and other objects will be apparent to those conversant with the art from the foregoing and subsequent descriptions.

According to the present invention, 2-ketoethyl-6,7-benzomorphan derivatives of the formula:

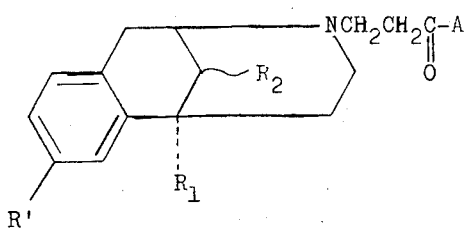

[I]

wherein R' is a hydrogen atom or a group of the formula: —OR'' (wherein R'' is a hydrogen atom, a $C_{1-5}$ alkanoyl group, a $C_{1-4}$ alkyl group, an aralkyl group such as $C_{7-11}$ phenylalkyl, a $C_{3-7}$ alkoxycarbonylmethyl group or a tetrahydropyranyl group), $R_1$ is a hydrogen atom, a $C_{1-5}$ alkyl group or a phenyl group substituted or unsubstituted with halogen, $C_{1-4}$ alkyl, $C_{1-4}$ alkoxy or trifluoromethyl, $R_2$ is a hydrogen atom or a $C_{1-4}$ alkyl group and A is a $C_{1-5}$ alkyl group, a $C_{1-5}$ alkoxy group, a phenyl group substituted or unsubstituted with halogen, $C_{1-4}$ alkyl, $C_{1-4}$ alkoxy or trifluoromethyl or a group of the formula:

(wherein $R_3$ and $R_4$ are independently a hydrogen atom or a $C_{1-4}$ alkyl group), and their pharmaceutically acceptable non-toxic salts, can be produced by reacting a 6,7-benzomorphan derivative of the formula:

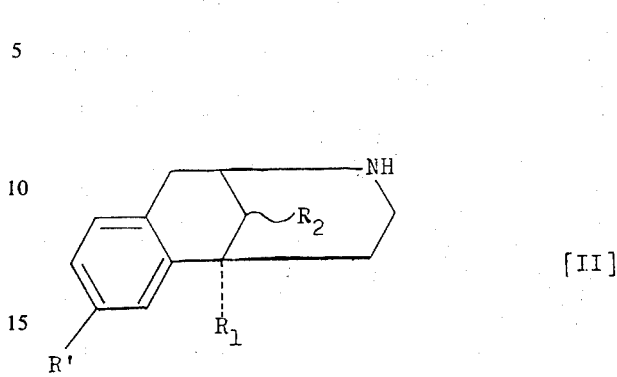

[II]

wherein R', $R_1$ and $R_2$ are each as defined above with a vinyl carbonyl compound of the formula:

[III]

wherein A is as defined above.

In the significances as defined above, examples of the alkyl group include methyl, ethyl, n-propyl, isopropyl, n-butyl, sec.-butyl, etc. As the alkoxy group, there may be exemplified methoxy, ethoxy, n-propoxy, isopropoxy, t-butoxy, etc. Examples of the alkanoyl group are formyl, acetyl, propionyl, butyryl, pentanoyl, etc. The aralkyl group may be benzyl, phenethyl, phenylpropyl or the like. The halogen atom includes fluorine, chlorine, bromine and iodine.

The reaction of the 6,7-benzomorphan derivative [II] with the vinyl carbonyl compound [III] is per se novel and may be called as the modified Michael Addition. The reaction is carried out in the absence or presence of an appropriate solvent (e.g. methanol, ethanol, ether, tetrahydrofuran, chloroform, dichloromethane, benzene, toluene, xylene, dimethylformamide). When desired, there may be used a catalyst, of which examples are N-benzyltrimethylammonium hydroxide (Triton B), sodium methoxide, sodium amide, potassium hydroxide, etc. The reaction proceeds at a temperature from about room temperature to the boiling point of the solvent as employed. By this reaction, the 2-ketoethyl-6,7-benzomorphan derivative [I] can be produced in an excellent yield and a high purity by a simple operation.

For the production of the 2-ketoethyl-6,7-benzomorphan derivative [I: R' = alkanoyloxy], the corresponding 2-ketoethyl-6,7-benzomorphan derivative [I: R' = hydroxyl] may be acylated by a per se conventional procedure, e.g. treating with an acid anhydride or an acyl halide.

When $R_2$ is alkyl, the 2-ketoethyl-6,7-benzomorphan derivative [I] has two stereo isomers, i.e. cis isomer ($R_2$ being α-configuration) and trans isomer ($R_2$ being β-configuration). Each of these isomers can be separated and purified by a per se conventional procedure such as fractional crystallization, fractional distillation or column chromatography. Alternatively, each of these isomers may be produced from the corresponding cis or trans-isomer of the 6,7-benzomorphan derivative [II] by reacting the same with the vinyl carbonyl compound [III]. Still, each of the said isomers has asymmetric carbon atoms, and there can be obtained four optically active isomers (i.e. (+)-cis, (−)-cis, (+)-trans, (−)-trans) by a conventional optical resolution procedure.

The 2-ketoethyl-6,7-benzomorphan derivative [I] possesses a basic nitrogen atom in the fundamental structure and hence various acid addition salts thereof can be formed. The acid addition salts can be obtained by the use of organic and inorganic acids such as formic acid, acetic acid, propionic acid, butyric acid, malic acid, fumaric acid, succinic acid, glutamic acid, tartaric acid, oxalic acid, citric acid, lactic acid, maleic acid, hydroxymaleic acid, glycolic acid, gluconic acid, glucuronic acid, saccharic acid, ascorbic acid, phenylacetic acid, benzoic acid, p-aminobenzoic acid, phthalic acid salicylic acid, anthranilic acid, p-hydroxybenzoic acid, p-aminosalicylic acid, picolinic acid, 3-hydroxy-2-naphthoic acid, 3-indoleacetic acid, barbituric acid, sulfamic acid, quininic acid, tropic acid, methanesulfonic acid, ethanesulfonic acid, benzenesulfonic acid, p-toluenesulfonic acid, hydroxyethanesulfonic acid, hydrofluoric acid, hydrochloric acid, hydrobromic acid, hydroiodic acid, perchloric acid, nitric acid, sulfuric acid, phosphoric acid and the like.

Examples of the 2-ketoethyl-6,7-benzomorphan derivatives [I] prepared by the present invention are as follows:

2'-Hydroxy-2-($\beta$-methylcarbonylethyl)-5,9-dimethyl-6,7-benzomorphan;

2'-Hydroxy-2-($\beta$-ethylcarbonylethyl)-5,9-dimethyl-6,7-benzomorphan;

2'-Hydroxy-2-($\beta$-methoxycarbonylethyl)-5,9-dimethyl-6,7-benzomorphan;

2'-Hydroxy-2-($\beta$-ethoxycarbonylethyl)-5,9-dimethyl-6,7-benzomorphan;

2'-Hydroxy-2-($\beta$-butoxycarbonylethyl)-5,9-dimethyl-6,7-benzomorphan;

2'-Hydroxy-2-($\beta$-aminocarbonylethyl)-5,9-dimethyl-6,7-benzomorphan;

2-($\beta$-Ethoxycarbonylethyl)-5,9-dimethyl-6,7-benzomorphan;

2'-Acetoxy-2-($\beta$-methoxycarbonylethyl)-5,9-dimethyl-6,7-benzomorphan;

2'-Methoxy-2-($\beta$-ethoxycarbonylethyl)-5,9-dimethyl-6,7-benzomorphan;

2'-Hydroxy-2-($\beta$-ethoxycarbonylethyl)-5-methyl-6,7-benzomorphan;

2'-Hydroxy-2-($\beta$-ethoxycarbonylethyl)-5-phenyl-6,7-benzomorphan;

2'-Hydroxy-2-($\beta$-p-fluorobenzoylethyl)-5,9-dimethyl-6,7-benzomorphan;

2'-Hydroxy-2-($\beta$-p-methoxybenzoylethyl)-5,9-dimethyl-6,7-benzomorphan, etc.

Among these 2-ketoethyl-6,7-benzomorphan derivatives [I], the ones wherein A is phenyl or substituted phenyl are known [cf. Belgian Patent No. 771,286].

Known 6,7-benzomorphan derivatives such as 2'-hydroxy-2,5,9-trimethyl-6,7-benzomorphan [cf. U.S. Pat. No. 3,138,603] have a potent analgesic activity but show an addiction liability. On account of this addiction liability, these analgesics are severely restricted in a therapeutic use. Surprisingly, the 2-ketoethyl-6,7-benzomorphan derivatives [I] (e.g. 2'-hydroxy-2-($\beta$-ethylcarbonylethyl)-5,9-dimethyl-6,7-benzomorphan, 2'-hydroxy-2-($\beta$-ethoxycarbonylethyl)-5,9-dimethyl-6,7-benzomorphan) do not show any addiction in long term animal tests. When, for example, these compounds were administered orally or subcutaneously to rats everyday for 4 weeks, the animals did not produce any physical dependency as shown in Table 1.

Table 1

| Compound | Dose (mg/kg/day) (mg/kg/day) | Abstinence syndrome |
|---|---|---|
| 2'-Hydroxy-2-($\beta$-ethylcarbonylethyl)-5,9-dimethyl-6,7-benzomorphan | 20 | − |
| 2'-Hydroxy-2-($\beta$-ethoxycarbonylethyl)-5,9-dimethyl-6,7-benzomorphan | 20 | − |
| 2'-Hydroxy-2,5,9-trimethyl-6,7-benzomorphan | 20 | ++ |
| Morphine | 20 | +++ |

Note: Groups of male rats of Wistar strain (body weight, 150 g at the beginning of the test), each group consisting of 20 male rats, were subcutaneously given the test compound twice a day for 4 consecutive weeks. On the next day after drug withdrawal, the body weight was measured. The symbols have the following meanings: +++, severe decrease (about 5% decrease); ++, moderate decrease; +, mild decrease; −, no decrease. The marked decrease is taken as an indication of the possession of a marcotic property by the test compound.

Further, the 2-ketoethyl-6,7-benzomorphan derivatives [I] show a strong analgesic activity. In a subcutaneous writhing test, for instance, they exhibited much more potent analgesic action than pentazocine (i.e. 2'-hydroxy-2-(3''-methyl-2''-butenyl)-5,9-dimethyl-6,7-benzomorphan), which is one of the strongest, commercial analgesics, as shown in Table 2.

Table 2

| Compound | $ED_{50}$ (mg/kg) |
|---|---|
| 2'-Hydroxy-2-($\beta$-ethylcarbonylethyl)-5,9-dimethyl-6,7-benzomorphan | 7.0 |
| 2'-Hydroxy-2-($\beta$-ethoxycarbonylethyl)-5,9-dimethyl-6,7-benzomorphan | 16.1 |
| Pentazocine | 17.5 |

Note: The test was based on the specific antagonism of the test compound to the typical syndrome produced by intraperitoneal injection of 0.6% aqueous acetic acid. The syndrome was characterized by intermittent contractions of the abdomen, twisting and turning of the trunk and extension of the hind legs. A group of 5 mice was used for each dose level. The test compound was administered subcutaneously 20 minutes before the injection of acetic acid. The number of mice which showed no pain response was recorded. The $ED_{50}$ value was calculated according to the Litchfield-Wilcoxon's method.

The pharmaceutical composition of the invention comprises an analgesically effective amount of the 2-ketoethyl-6,7-benzomorphan derivative [I] as an active ingredient and a pharmaceutically acceptable carrier or diluent.

The 2-ketoethyl-6,7-benzomorphan derivatives [I] may be prepared for use by dissolving under sterile conditions a salt form of them in water (or an equivalent or more amount of a pharmaceutically acceptable acid if the free base is used instead of the salt), or in a physiologically compatible aqueous medium such as saline, and stored in ampoules for use by injection. Alternatively, they can be incorporated in unit dosage (1-30 mg) form as tablets or capsules for oral administration either alone or in combination with suitable adjuvants such as calcium carbonate, starch, lactose, talc, magnesium stearate and gum acacia.

Practical and presently preferred embodiments of the present invention are shown in the following Examples. Modifications of the procedures shown in these Examples will be obvious to those skilled in the art, and these Examples do not limit the scope of the invention.

EXAMPLE 1

2'-Hydroxy-2-(β-ethoxycarbonylethyl)-5,9-dimethyl-6,7-benzomorphan

2'-Hydroxy-5,9-dimethyl-6,7-benzomorphan (1.0 g) is dissolved in 50 ml of hot ethanol. After the solution is cooled to room temperature, 0.5 g of ethyl acrylate is added thereto. The mixture is stirred at room temperature for 30 minutes and then refluxed for 20 minutes. Concentration to dryness followed by addition of a small amount of acetone gives crystals. Recrystallization from acetone yields 2'-hydroxy-2-(β-ethoxycarbonylethyl)-5,9-dimethyl-6,7-benzomorphan. M.P. 136° to 138°C. IR$\nu_{paraffin}^{cm^{-1}}$: 1715.

Anal. Calcd. for $C_{19}H_{27}NO_3$: C, 71.89%; H, 8.57%; N, 4.41%. Found: C, 71.81%; H, 8.41%; N, 4.49%.

EXAMPLE 2

2'-Hydroxy-2-(β-methoxycarbonylethyl)-5,9-dimethyl-6,7-benzomorphan

2'-Hydroxy-5,9-dimethyl-6,7-benzomorphan (3.0 g) is dissolved in 50 ml of hot methanol. After the solution is cooled to room temperature, 10 ml of methyl acrylate are added thereto. The mixture is allowed to stand at room temperature for 4 hours and concentrated to dryness. The crude product is recrystallized from methanol to yield 2'-hydroxy-2-(β-methoxycarbonylethyl)-5,9-dimethyl-6,7-benzomorphan. M.P. 154° to 156°C. IR$\nu_{paraffin}^{cm^{-1}}$: 1715.

Anal. Calcd. for $C_{18}H_{25}NO_3$: C, 71.25%; H, 8.31%; N, 4.62%. Found: C, 71.42%; H, 8.48%; N, 4.72%.

EXAMPLE 3

2'-Hydroxy-2-(β-aminocarbonylethyl)-5,9-dimethyl-6,7-benzomorphan

To a solution of 1.1 g of 2'-hydroxy-5,9-dimethyl-6,7-benzomorphan in 50 ml of absolute ethanol is added 0.4 g of acrylamide. The resultant mixture is refluxed for 1 hour and concentrated to dryness. The crude product is recrystallized from acetone to yield 2'-hydroxy-2-(β-aminocarbonylethyl)-5,9-dimethyl-6,7-benzomorphan. M.P. 105° to 108°C (decomp.). IR$\nu_{paraffin}^{cm^{-1}}$: 1660.

Anal. Calcd. for $C_{17}H_{24}N_2O_2$: C, 70.80%; H, 8.39%; N, 9.71%. Found: C, 70.75%; H, 8.62%; N, 9.40%.

EXAMPLE 4

2'-Hydroxy-2-(β-n-butoxycarbonylethyl)-5,9-dimethyl-6,7-benzomorphan

To a solution of 1.1 g of 2'-hydroxy-5,9-dimethyl-6,7-benzomorphan in 30 ml of methanol is added 0.7 g of n-butyl acrylate. The resultant mixture is refluxed for 1 hour and treated in accordance with the manner similar to that of Example 1 to yield 2'-hydroxy-2-(β-n-butoxycarbonylethyl)-5,9-dimethyl-6,7-benzomorphan. M.P. 152° to 154°C (decomp.). IR$\nu_{paraffin}^{cm^{-1}}$: 1715.

Anal. Calcd. for $C_{21}H_{31}NO_3$: C, 73.00%; H, 9.05%; N, 4.05%. Found: C, 72.58%; H, 9.40%; N, 4.31%.

EXAMPLE 5

2'-Hydroxy-2-(β-ethylcarbonylethyl)-5,9-dimethyl-6,7-benzomorphan

To a solution of 1.1 g of 2'-hydroxy-5,9-dimethyl-6,7-benzomorphan in 30 ml of methanol is added 0.5 g of ethyl vinyl ketone. The resultant mixture is refluxed for 1 hour and concentrated to dryness. The crude product is recrystallized from acetone-ethyl acetate to yield 2'-hydroxy-2-(β-ethylcarbonylethyl)-5,9-dimethyl-6,7-benzomorphan. M.P. 133° to 134°C. IR$\nu_{paraffin}^{cm^{-1}}$: 1710.

Anal. Calcd. for $C_{19}H_{27}NO_3$: C, 75.71%; H, 9.03%; N, 4.65%. Found: C, 75.59%; H, 8.94%; N, 4.53%.

EXAMPLES 6 to 12

The following compounds are obtained in accordance with the manner similar to that of Example 5:

2'-Hydroxy-2-(β-methylcarbonylethyl)-5,9-dimethyl-6,7-benzomorphan, M.P. 130° to 132°C;

2'-Hydroxy-2-(β-p-methoxybenzoylethyl)-5,9-dimethyl-6,7-benzomorphan, M.P. 172° to 175°C;

2'-Hydroxy-2-(β-p-fluorobenzoylethyl)-5,9-dimethyl-6,7-benzomorphan, M.P. 156.5° to 160°C;

2-(β-p-Fluorobenzoylethyl)-5-phenyl-6,7-benzomorphan hydrochloride, M.P. 163° to 166°C;

2'-Hydroxy-2-(β-benzoylethyl)-5,9-dimethyl-6,7-benzomorphan, M.P. 164° to 167°C;

2-(β-p-Fluorobenzoylethyl)-5-methyl-6,7-benzomorphan hydrochloride, M.P. 177° to 178°C;

2'-Hydroxy-2-(β-p-fluorobenzoylethyl)-6,7-benzomorphan, M.P. 155° to 159°C.

What is claimed is:

1. A benzomorphan derivative of the formula:

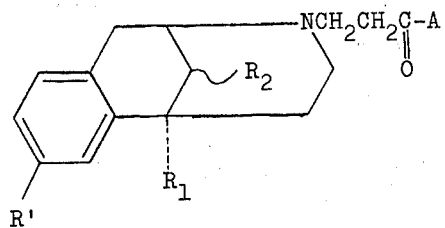

wherein R' is a hydrogen atom or a group of the formula: —OR'', wherein R'' is a hydrogen atom, a $C_{1-5}$ alkanoyl group, a $C_{1-4}$ alkyl group, a $C_7$-$C_{11}$ phenylalkyl group, a $C_{3-7}$ alkoxycarbonylmethyl group or a tetrahydropyranyl group, $R_1$ is a hydrogen atom, a $C_{1-5}$ alkyl group or a phenyl group substituted or unsubstituted with halogen, $C_{1-4}$ alkyl, $C_{1-4}$ alkoxy or trifluoromethyl, $R_2$ is a hydrogen atom or a $C_{1-4}$ alkyl group and A is a $C_{1-5}$ alkyl group, a $C_{1-5}$ alkoxy group or a group of the formula:

wherein $R_3$ and $R_4$ are independently a hydrogen atom or a $C_{1-4}$ alkyl group, and its pharmaceutically acceptable non-toxic salts.

2. The benzomorphan derivative of claim 1, wherein $R_2$ is alkyl.

3. 2'-Hydroxy-2-($\beta$-ethoxycarbonylethyl)-5,9-dimethyl-6,7-benzomorphan.

4. 2'-Hydroxy-2-($\beta$-aminocarbonylethyl)-5,9-dimethyl-6,7-benzomorphan.

5. 2'-Hydroxy-2-($\beta$-ethylcarbonylethyl)-5,9-dimethyl-6,7-benzomorphan.

6. The benzomorphan derivative of claim 1, namely 2'-hydroxy-2-($\beta$-n-butoxycarbonylethyl)-5,9-dimethyl-6,7-benzomorphan.

7. The benzomorphan derivative of claim 1, namely 2'-hydroxy-2-($\beta$-ethylcarbonylethyl)-5,9-dimethyl-6,7-benzomorphan.

8. The benzomorphan derivative of claim 1, namely 2'-hydroxy-2-($\beta$-methylcarbonylethyl)-5,9-dimethyl-6,7-benzomorphan.

9. The benzomorphan derivative of claim 1, namely 2'-hydroxy-2-($\beta$-p-methoxybenzoylethyl)-5,9-dimethyl-6,7-benzomorphan.

10. The benzomorphan derivative of claim 1, namely 2'-hydroxy-2-($\beta$-p-fluorobenzoylethyl)-5,9-dimethyl-6,7-benzomorphan.

11. The benzomorphan derivative of claim 1, namely 2-($\beta$-1-fluorobenzoylethyl)-5-phenyl-6,7-benzomorphan hydrochloride.

12. The benzomorphan derivative of claim 1, namely 2'-hydroxy-2-($\beta$-benzoylethyl)-5,9-dimethyl-6,7-benzomorphan.

13. The benzomorphan derivative of claim 1, namely 2-($\beta$-p-fluorobenzoylethyl)-5-methyl-6,7-benzomorphan hydrochloride.

14. The benzomorphan derivative of claim 1, namely 2'-hydroxy-2-($\beta$-p-fluorobenzoylethyl)-6,7-benzomorphan.

15. A process for producing benzomorphan derivatives of the formula:

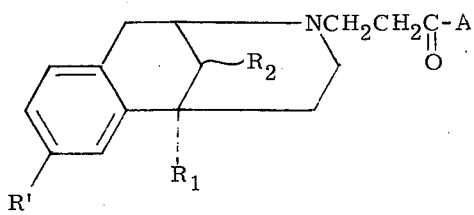

wherein R' is a hydrogen atom or a group of the formula: —OR'' wherein R'' is a hydrogen atom, a $C_{1-5}$ alkanoyl group, a $C_{1-4}$ alkyl group, an aralkyl group, a $C_{3-7}$ alkoxycarbonylmethyl group or a tetrahydropyranyl group, $R_1$ is a hydrogen atom, a $C_{1-5}$ alkyl group or a phenyl group substituted or unsubstituted with halogen, $C_{1-4}$ alkyl, $C_{1-4}$ alkoxy or trifluoromethyl, $R_2$ is a hydrogen atom or a $C_{1-4}$ alkyl group and A is a $C_{1-5}$ alkyl group, a $C_{1-5}$ alkoxy group, a phenyl group substituted or unsubstituted with halogen, $C_{1-4}$ alkyl, $C_{1-4}$ alkoxy or trifluoromethyl or a group of the formula:

wherein $R_3$ and $R_4$ are independently a hydrogen atom or a $C_{1-4}$ alkyl group, or their pharmaceutically acceptable non-toxic salts, which comprises reacting a 6,7-benzomorphan derivative of the formula:

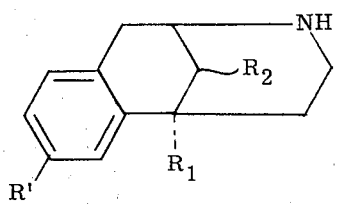

wherein R', $R_1$ and $R_2$ are each as defined above with a vinyl carbonyl compound of the formula:

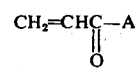

wherein A is as defined above in the presence of a catalyst selected from the group consisting of N-benzyltrimethylammonium hydroxide, sodium methoxide, sodium amide and potassium hydroxide.

16. The process according to claim 15, wherein the reaction is carried out in the presence of a solvent.

17. The process according to claim 16, wherein the solvent is methanol, ethanol, ether, tetrahydrofuran, chloroform, dichloromethane, benzene, toluene, xylene or dimethylformamide.

18. The process according to claim 15, wherein the reaction is carried out at a temperature within a range between room temperature and the boiling point of the solvent.

19. The process according to claim 15, wherein the reaction is carried out in the absence of a solvent.

20. The process according to claim 15, wherein said vinyl carbonyl compound is selected from the group consisting of ethyl acrylate, methyl acrylate, acrylamide and butyl acrylate.

* * * * *